(12) United States Patent
Kitazume et al.

(10) Patent No.: US 8,609,346 B2
(45) Date of Patent: Dec. 17, 2013

(54) METHOD FOR DIAGNOSING ALZHEIMER'S DISEASE USING SERUM GLYCOPROTEIN AS BIOMARKER

(75) Inventors: Shinobu Kitazume, Wako (JP); Ritsuko Oka, Wako (JP); Yasuhiro Hashimoto, Wako (JP); Yuji Sato, Wako (JP); Keiko Sato, legal representative, Tokyo (JP); Tamao Endo, Wako (JP); Makoto Higuchi, Wako (JP); Hiroyuki Arai, Wako (JP); Takaomi Saido, Wako (JP)

(73) Assignee: Riken, Saitama (JP)

( * ) Notice: Subject to any disclaimer, the term of this patent is extended or adjusted under 35 U.S.C. 154(b) by 1040 days.

(21) Appl. No.: 11/920,167

(22) PCT Filed: May 11, 2006

(86) PCT No.: PCT/JP2006/309450
§ 371 (c)(1),
(2), (4) Date: Nov. 17, 2010

(87) PCT Pub. No.: WO2006/121099
PCT Pub. Date: Nov. 16, 2006

(65) Prior Publication Data
US 2011/0076704 A1 Mar. 31, 2011

(30) Foreign Application Priority Data
May 11, 2005 (JP) ................. 2005-138070

(51) Int. Cl.
*G01N 33/53* (2006.01)
*G01N 33/96* (2006.01)

(52) U.S. Cl.
USPC ..................................... 435/7.1

(58) Field of Classification Search
None
See application file for complete search history.

(56) References Cited

U.S. PATENT DOCUMENTS

| 7,838,634 B2 * | 11/2010 | Haab et al. .............. 530/387.1 |
| 2007/0099203 A1 * | 5/2007 | Zhang ............................ 435/6 |
| 2009/0166224 A1 * | 7/2009 | Yang et al. ..................... 205/792 |

OTHER PUBLICATIONS

Hanasaki K et al. Binding of human plama sialoglycoproteins by the B cell-specific lectin CD22. J Biol Chem. 1995; 270(13:7543-7550.*
Katnik I et al. Development of concanavalin A-enzyme immunosorbent assay for glycated haptoglobin using polyclonal and monoclonal antibodies. J Immunoassay. 1992; 13(2):145-162.*
Ulloa F et al. Differential distribution of sialic acid in alpha2,3 and alpha2,6 linkages in the apical membrane of cultured epithelial cells and tissues. J Histochem Cytochem. 2001; 49(4):501-509.*
Matsumoto H et al. (2010) Clinical application of a lectin-antibody ELISA to measure fucosylated haptoglobin in sera of patients with pancreatic cancer. Clin. Chem. Lab. Med. 48(4):505-512.*
Reid DM et al. (1990) Western blot identification of platelet proteins that bind normal serum immunoglobulins. Characteristics of a 95-Kd reactive protein. Blood, 75(11):2194-2203.*
Valentine MA et al. (1988) Antibody to a novel 95-kDa surface glycoprotein on human B cells induces calcium mobilization and B cell activation. J. Immunol. 140(12):4071-4078.*
Buxbaum, J.D., et al. "Evidence That Tumor Necrosis Factor α Converting Enzyme Is Involved in Regulated α-Secretase Cleavage of the Alzheimer Amyloid Protein Precursor," J. Biol. Chem., vol. 273, No. 43, pp. 27765-27767 (1998).
Iwata, N., et al., "Metabolic Regulation of Brain Aβ by Neprilysin," Science, vol. 292, pp. 1550-1552 (2001).
Lammich, S., et al., Constitutive and regulated α-secretase cleavage of Alzheimer's amyloid precursor protein by a disintegrin metalloprotease, Proc. Natl. Acad. Sci., vol. 96, pp. 3922-3927 (1999).
Selkoe, D. J., "Alzheimer's Disease: Genes, Proteins, and Therapy," Physiol. Rev., vol. 81, No. 2, pp. 741-766 (2001).
De Strooper, B., et al., "Deficiency of presenilin-1 inhibits the normal cleavage of amyloid precursor protein," Nature, vol. 391, pp. 387-390 (1998).
Wolfe, M.S., "Two transmembrane aspartates in presenilin-1 required for presenilin endoproteolysis and γ-secretase activity," Nature, vol. 398, pp. 513-517 (1999).
Yasukawa, et al., Inflammation-dependent changes in α2,3-, α2,6-, and α2,8-sialic acid glycotopes on serum glycoproteins in mice, Glycobiology vol. 15 No. 9 pp. 827-837, 2005.
Aisen, et al., Inflammatory Mechanisms in Alzheimer's Disease: Implications for Therapy, Am J Psychiatry 1994, vol. 151, pp. 1105-1113.
Kitazume, et al., Alzheimer's β-secretase, β-site amyloid precursor protein-cleaving enzyme, is responsible for cleavage secretion of a Golgi-resident sialyltransferase, PNAS (2001) vol. 98, No. 24, pp. 13554-13559.
Johnson et al., Applied and Theoretical Electrophoresis, vol. 3, 1992, pp. 47-53.
Spagnuolo et al., Biol. Chem., vol. 384, 2003, pp. 1593-1596.
Kitazume et al., Glycoconjugate Journal, vol. 20, 2004, pp. 59-62.
Kitazume et al, The Journal of Biological Chemistry, vol. 280, No. 9, Mar. 2005, pp. 8589-8595.

* cited by examiner

*Primary Examiner* — Kimberly A Ballard
(74) *Attorney, Agent, or Firm* — Birch, Stewart, Kolasch & Birch, LLP.

(57) ABSTRACT

It is an object of the present invention to detect a change in the metabolism of a glycoprotein having an α2,6-sialyl residue, which is contained in blood, so as to provide an agent and a method for diagnosing sporadic Alzheimer's disease. The present invention provides an agent for diagnosing Alzheimer's disease, which comprises lectin used for detecting an α2,6-sialyl residue-containing glycoprotein.

5 Claims, 2 Drawing Sheets

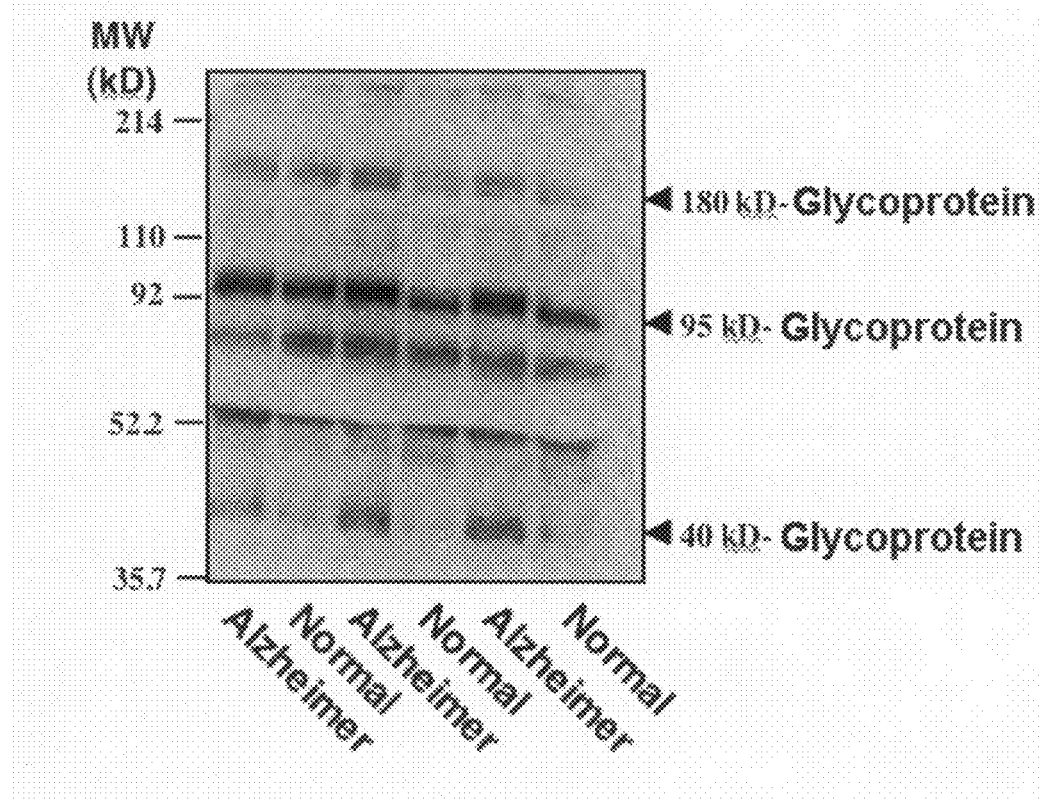

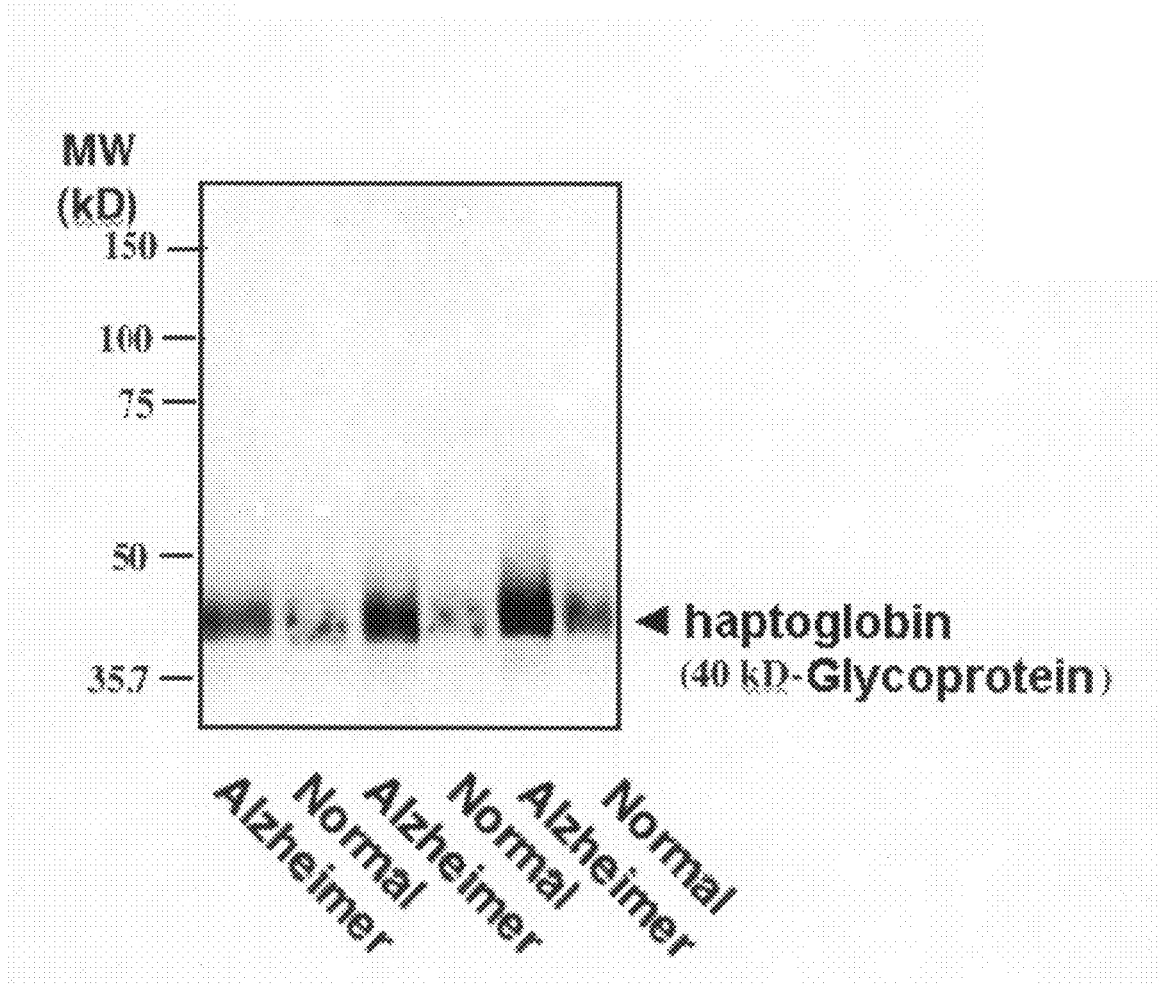

METHOD FOR DIAGNOSING ALZHEIMER'S DISEASE USING SERUM GLYCOPROTEIN AS BIOMARKER

This application is the national stage of International application PCT/JP2006/309450, filed in Japan on May 11, 2006, and claims priority under 35 USC §119(a)-(d) of Japanese application 2005-138070 filed in Japan on May 11, 2005.

TECHNICAL FIELD

The present invention relates to an agent and a method for diagnosing Alzheimer's disease. More specifically, the present invention relates to an agent and a method for diagnosing Alzheimer's disease, in which an α2,6-sialyl residue-containing glycoprotein is used as a marker.

BACKGROUND ART

Alzheimer's disease is a disease attended with a wide range of symptoms of neurodegenerative dementia. Generation of amyloid β peptides (Aβ) is considered to be a cause of Alzheimer's disease (Selkoe, D. J. (2001) Physiol. Rev. 81, 741-766; and Iwata, N. et al., (2001) Science 292, 1550-1552). An amyloid precursor protein (APP) is cleaved with β-secretase, and as a result, a soluble $NH_2$-terminal fragment (APPsβ) and a 12-kDa COOH-terminal fragment (C99) are generated. The latter fragment remains bound to a membrane. C99 is further cleaved with γ-secretase, and then pathogenic Aβ is generated (De Strooper, B. et al., (1998) Nature (London) 391, 387-390; and Wolfe, M. S. et al., (1990) Nature (London) 398, 513-517.) Via another pathway, APP is cleaved with α-secretase in an Aβ sequence, and as a result, a soluble $NH_2$-terminal fragment (APPsα) and a 10-kDa membrane-bound COOH-terminal fragment (C83) are generated (Buxbaum, J. D. et al., (1998) J. Biol. Chem. 273, 27765-27767; and Lammich, S. et al., (1999) Proc. Natl. Acad. Sci. USA 96, 3922-3927).

It has been reported that there are a large number of markers showing a correlation with Alzheimer's disease. The relationship of a majority of such markers with the pathological changes is unknown, and the diagnostic value has not been necessarily established. Markers that are directly associated with such pathological changes include a decrease in one type of amyloid β peptide (Aβ 1-42) consisting of 42 amino acids contained in cerebrospinal fluid. However, since such Aβ peptide is easily aggregated to create a precipitate, it becomes a cause of diseases. Accordingly, the amount of free Aβ is very small, and thus it is theoretically difficult to use such a trace amount of Aβ as a diagnostic marker. As a matter of fact, it has been known that the amount of such Aβ peptide is fluctuated only after the symptoms of Alzheimer's disease become severe. Thus, such Aβ peptide cannot be used as an early diagnostic marker. On the other hand, an increase of the phosphorylated tau protein in cerebrospinal fluid is observed even at an early stage of the disease, and thus it is considered the most excellent biomarker. However, when such phosphorylated tau is increased, neuron death has already progressed. Accordingly, even if a treatment is initiated at such stage, a complete recovery of nerve function cannot be expected. In addition, when such markers are used in measurements using cerebrospinal fluid (lumbar puncture fluid). In order to collect such material, a special technique is necessary. Since it puts a burden upon patients, a method using the aforementioned markers cannot become a mass screening method.

The present inventors have found that β-secretase cleaves not only an amyloid precursor protein, but also α2,6-sialyltransferase. Based on this discovery, the inventors have measured the cleaved free α2,6-sialyltransferase. Thereafter, regarding the fact that such α2,6-sialyltransferase can be used in diagnoses as a marker for an increase in β-secretase activity, the inventors have previously filed a patent application (Japanese Patent Application No. 2003-382374, which has been unpublished at the time of filing of the present application). In the aforementioned patent application, an antibody that specifically recognizes the cleavage site of human soluble α2,6-sialyltransferase is used. Use of this antibody has enabled quantification of soluble α2,6-sialyltransferase in human blood or cerebrospinal fluid. Thus, a method for monitoring β-secretase activity has been provided. However, in general, only a trace amount of glycosyltransferase is contained in body fluid, and thus the detection efficiency is not necessarily high. Further, a cleavage site-recognizing antibody has been required for detection of such glycosyltransferase.

DISCLOSURE OF THE INVENTION

Problems to be Solved by the Invention

In sporadic Alzheimer's disease, which accounts for 95% or more of all types of Alzheimer's diseases, Alzheimer's disease β-secretase activity is increased, and the cleavage of an amyloid precursor protein with this enzyme increasingly takes place. As a result, generation of an amyloid β peptide (Aβ) that is a final product is increased, and it is then precipitated in the brain. This precipitate is called senile plaque, which is considered to be a pathologic change in the early stage of Alzheimer's disease. That is to say, an increase in the activity of β-secretase triggers sporadic Alzheimer's disease. If changes in such β-secretase activity can be detected, the aforementioned disease can be diagnosed before the development thereof, and thus it becomes possible to effectively prevent such disease. However, to date, such a method for easily detecting such activity increase with high sensitivity has not previously existed.

It is an object of the present invention to detect a change in the metabolism of a glycoprotein having an α2,6-sialyl residue, which is contained in blood, so as to provide an agent and a method for diagnosing sporadic Alzheimer's disease.

Means for Solving the Problems

As a result of intensive studies directed towards achieving the aforementioned object, the present inventors have found that β-secretase cleaves not only an amyloid precursor protein, but also α2,6-sialyltransferase, and that the metabolism of a glycoprotein having an α2,6-sialyl residue that is an enzyme product thereof is changed. Thereafter, the inventors have used lectins specifically binding to α2,6-sialyl residues (SNA, SSA, and TJA lectins, etc.) to examine changes in such glycoproteins contained in the blood of a patient suffering from Alzheimer's disease. As a result, the inventors have revealed that the quantities of several glycoproteins had been changed (refer to Example 1). This result demonstrated that an α2,6-sialyl residue-containing glycoprotein can be used as a marker in the diagnosis of Alzheimer's disease.

That is to say, the present invention provides an agent for diagnosing Alzheimer's disease, which comprises lectin used for detecting an α2,6-sialyl residue-containing glycoprotein.

The α2,6-sialyl residue-containing glycoprotein is preferably a 180-kD glycoprotein, a 95-kD glycoprotein, or a 40-kD glycoprotein.

In another aspect, the present invention provides an agent for diagnosing Alzheimer's disease, which comprises an anti-haptoglobin antibody used for detecting a 40-kD glycoprotein that contains α2,6-sialyl residue.

In a further aspect, the present invention provides a kit for diagnosing Alzheimer's disease, which comprises lectin and an anti-haptoglobin antibody.

In a further aspect, the present invention provides a method for diagnosing Alzheimer's disease, which comprises detecting or measuring an α2,6-sialyl residue-containing glycoprotein contained in a human-derived sample.

Preferably, the α2,6-sialyl residue-containing glycoprotein is a 180-kD glycoprotein, a 95-kD glycoprotein, or a 40-kD glycoprotein.

Preferably, the α2,6-sialyl residue-containing glycoprotein is detected or measured by using lectin.

Preferably, a 40-10 glycoprotein that contains α2,6-sialyl residue is detected or measured by using an anti-haptoglobin antibody.

Preferably, a 40-kD glycoprotein that contains α2,6-sialyl residue is detected or measured by sandwich assay using lectin and an anti-haptoglobin antibody.

The human-derived sample is preferably a blood sample.

BEST MODE FOR CARRYING OUT THE INVENTION

The embodiments of the present invention will be described in detail below.

The agent and method for diagnosing Alzheimer's disease of the present invention is characterized in that an α2,6-sialyl residue-containing glycoprotein is used as a marker. More specifically, a 180-kD glycoprotein, a 95-kD glycoprotein, or a 40-kD glycoprotein, which contains sialic acid, can be used as a marker. All of such glycoproteins can be detected using lectin. In addition, the 40-kD glycoprotein can be detected using an anti-haptoglobin antibody.

As an example of the diagnostic method of the present invention, the amount of an α2,6-sialyl residue-containing glycoprotein existing in a subject-derived sample is compared with the amount of an α2,6-sialyl residue-containing glycoprotein existing in a sample derived from a control subject, so as to diagnose Alzheimer's disease.

Such an α2,6-sialyl residue-containing glycoprotein (preferably, a 180-kD glycoprotein, a 95-kD glycoprotein, or a 40-kD glycoprotein) can be detected or measured by an assay using lectin or an antibody that specifically recognizes the α2,6-sialyl residue-containing glycoprotein (for example, an anti-haptoglobin antibody that can be used for the 40-kD glycoprotein).

That is, the binding of an α2,6-sialyl residue-containing glycoprotein with lectin or the aforementioned antibody can be analyzed by binding a labeling substance used for enzyme labeling, color labeling, radiolabeling, or luminescent labeling, etc., to lectin, the aforementioned antibody, or a secondary antibody, and then detecting or measuring such a labeling substance. Examples of an immunoassay that can be carried out in the present invention include ELISA, Western blotting, immunoprecipitation, slot or dot blot assay, immunohistological staining, radio immuno assay (RIA), fluoroimmunoassay, and an immunoassay using an avidin-biotin or streptoavidin-biotin system, but examples are not limited thereto.

A human-derived sample can be used in the diagnostic method of the present invention. The type of such a human-derived sample is not particularly limited, as long as an α2,6-sialyl residue-containing glycoprotein (preferably, a 180-kD glycoprotein, a 95-kD glycoprotein, or a 40-kD glycoprotein) can be detected or measured in the sample. Examples of such a human-derived sample used herein include blood (serum, plasma, etc.), urine, saliva, and a brain-derived sample. A preferred example is blood (serum or plasma).

The type of lectin used in the present invention is not particularly limited, as long as it recognizes such an α2,6-sialyl residue-containing glycoprotein and detects it. Examples of such lectin used herein include SNA lectin (*Sambucus nigra* lectin), SSA lectin (*Sambucus sieboldiana* lectin), and TJA lectin (*Trichosanthes japonica* lectin). The lectin used in the present invention may be labeled, as necessary. As the labeling substance, a labeling substance for a labeled antibody as described later in the present specification can be used.

An example of the antibody used in the present invention is an anti-haptoglobin antibody. It has been known that haptoglobin is fluctuated when acute inflammation or hemolytic anemia occurs. Accordingly, it is necessary to make the differential diagnosis between the aforementioned diseases and Alzheimer's disease. Acute inflammation can be differentiated by a common biochemical examination of blood such as the use of a C reactive protein value. Hemolytic anemia can be differentiated by a common examination used for icterus, hyperbilirubinemia, or the like. In the case of hemolytic anemia, advanced examinations such as the measurement of erythrocyte life span or the measurement of iron metabolism cycle may be necessary in some cases. However, such advanced examinations are carried out only in extremely exceptional cases. That is, Alzheimer's disease can be easily differentiated from the aforementioned diseases by a common biochemical examination with blood specimen, and thus the use of an anti-haptoglobin antibody does not become an impediment to the diagnosis of Alzheimer's disease.

Moreover, in the case of a 180-kD glycoprotein and a 95-kD glycoprotein, such a glycoprotein is purified, and thereafter, an animal is immunized with the glycoprotein or a partial peptide thereof used as an antigen, so as to obtain an antibody. The antibody used in the present invention can be either a polyclonal antibody or a monoclonal antibody. Such an antibody can be produced by common methods.

In the case of a polyclonal antibody, for example, a mammal is immunized with the aforementioned protein or a partial peptide thereof used as an antigen, and blood is then collected from the mammal. Thereafter, an antibody can be separated and purified from the collected blood. For example, mammals such as a mouse, a hamster, a guinea pig, a chicken, a rat, a rabbit, a dog, a goat, a sheep, or a bovine can be immunized. As an immunization method, a common immunization method known to persons skilled in the art may be used, and an antigen may be administered one or more times, for example.

Such an antigen can be administered two or three times at intervals of 7 to 30 days, and particularly 12 to 16 days. As a single dose, approximately 0.05 to 2 mg of antigen can be administered, for example. Also, an administration route is not particularly limited. Subcutaneous administration, intracutaneous administration, intraperitoneal administration, intravenous administration, intramuscular administration, or the like can be selected, as appropriate. It is preferable to administer an antigen via an intravenous, intraperitoneal, or subcutaneous administration route. Furthermore, such an antigen can be dissolved in a suitable buffer that contains a commonly used adjuvant such as a complete Freund's adjuvant, RAS [MPL (Monophosphoryl Lipid A)+TDM (Synthetic Trehalose Dicorynomycolate)+CWS (Cell Wall Skeleton) adjuvant system], or aluminum hydroxide, before use. However, there may also be cases where the aforementioned adjuvants cannot be used depending on an administration route, other administration conditions, etc. The term "adjuvant" is used herein to mean a substance, which is administered together with an antigen and which non-specifically enhances an immune reaction to the antigen.

An immunized mammal is raised for 0.5 to 4 months. Thereafter, a small amount of serum is collected as a sample from the ear vein of the mammal, and an antibody titer thereof can be then measured. If such an antibody titer is increased, an antigen is administered for a suitable number of times depending on the situation. A booster can be carried out with 10 to 1,000 µg of antigen, for example. One to two months after the final administration, blood is collected from the immunized mammal according to an ordinary method, and it is then treated at 56° C. for 30 minutes to inactivate a complement system. Thereafter, a specific antibody is purified by affinity chromatography. As an affinity carrier, an antigen peptide that has been immobilized on Affigel or the like can be used, for example. The aforementioned blood is separated and purified by an ordinary method such as centrifugation, precipitation using ammonium sulfate or polyethylene glycol, or chromatography such as gel filtration chromatography, ion exchange chromatography or affinity chromatography, so as to obtain a polyclonal antibody in the form of a polyclonal antiserum. It is to be noted that such serum may be treated at 56° C. for 30 minutes to inactivate a complement system.

A monoclonal antibody can be produced using a hybridoma obtained by the cell fusion between an antibody-generating cell and a myeloma cell line. A hybridoma that generates a monoclonal antibody can be obtained by the following cell fusion method.

As antibody-generating cells, splenic cells, lymph node cells, B lymphocytes, or other types of cells, obtained from the immunized animal, can be used. As an antigen, the same protein or peptide as in the case of a polyclonal antibody can be used. As an animal to be immunized, a mouse, a rat, or the like can be used. An antigen is administered to such animals according to common methods. For example, a suspension or an emulsion is prepared by mixing an adjuvant such as a complete Freund's adjuvant or an incomplete Freund adjuvant with an antigen peptide. Thereafter, the thus prepared suspension or emulsion is administered intravenously, subcutaneously, intracutaneously, intraperitoneally, etc., to an animal to be immunized several times, so that the animal can be immunized. Thereafter, antibody-generating cells such as splenic cells are obtained from the thus immunized animal, and the obtained splenic cells are then fused with myeloma cells according to a known method (G. Kohler et al., Nature, 256 495 (1975)), so as to produce hybridomas.

Examples of a myeloma cell line used in cell fusion include P3X63Ag8, P3U1 line, and Sp2/0 line, in the case of mice. When cell fusion is carried out, a fusion promoter such as polyethylene glycol or Sendai virus is used. In order to select hybridomas after completion of the cell fusion, a hypoxanthine-aminopterin-thymidine (HAT) medium can be used according to common methods. Hybridomas obtained as a result of the cell fusion can be cloned by the limiting dilution method or the like. Further, the obtained cells are screened by enzyme immunoassay or the like, so as to obtain a cell line that generates a monoclonal antibody capable of specifically recognizing an α2,6-sialyl residue-containing glycoprotein.

In order to produce a monoclonal antibody of interest from the thus obtained hybridomas, the hybridomas may be cultured by a common cell culture method or an ascites formation method, and the monoclonal antibody may be purified from the culture supernatant or ascites. Such monoclonal antibody can be purified from such culture supernatant or ascites according to common methods. For example, methods such as ammonium sulfate fractionation, gel filtration, ion exchange chromatography, and affinity chromatography can be used in combination, as appropriate.

The antibody used in the present invention can also be used as a labeled antibody. By producing such a labeled antibody, an α2,6-sialyl residue-containing glycoprotein can be easily detected or measured. In addition, the antibody of the present invention, or a secondary antibody that binds to an α2,6-sialyl residue-containing glycoprotein as an antigen thereof, can also be labeled before use. The type of labeling substance for the antibody of the present invention or the secondary antibody thereof, and a labeling method thereof, can be appropriately selected from those known to persons skilled in the art.

When an enzyme is used as a labeling substance, horseradish peroxidase, alkaline phosphatase, glucose oxidase, β-galactosidase, glucoamylase, carbonic anhydrase, acetylcholine esterase, lysozyme, malate dehydrogenase, glucose-6-phosphate dehydrogenase, or the like can be used as such a labeling substance. Examples of a method of labeling the antibody of the present invention, the secondary antibody thereof, or the fragment thereof (F(ab')2 fragment, Fab' fragment, etc.) with such enzyme include: a method comprising oxidizing a sugar chain of enzyme with periodic acid and allowing the amino acid of the aforementioned antibody or the like to bind to the generated aldehyde group; and a method of introducing a maleimide group, a pyridyl sulfide group or the like into the enzyme and allowing such a group to bind to a thiol group existing in the Fab' fragment of the aforementioned antibody.

When an enzyme is used as a labeling substance, a test sample and a labeled antibody are subjected to incubation. Thereafter, a free labeled antibody is eliminated by washing, and the substrate of the aforementioned labeling enzyme is then allowed to act thereon. The reaction is measured based on color development or the like, so that the labeled antibody can be detected. When an antibody is labeled with peroxidase for example, hydrogen peroxide used as a substrate is combined with diaminobenzidine or O-phenylenediamine used as a coloring agent, so as to generate a brown or yellow color. When an antibody is labeled with glucoseoxidase, 2,2'-azino-di-(3-ethylbenzothiazolin-6-sulfonate) (ABTS) can be used as a substrate, for example.

When a fluorochrome is used as a labeling substance, the antibody of the present invention or a secondary antibody thereof can be labeled with a fluorochrome such as FITC (fluorescein isothiocyanate) or TRITC (tetramethylrhodamine B isothiocyanate). The antibody of the present invention or a secondary antibody thereof can be bound to a fluorochrome by a common method.

When a coloring substance is used as a labeling substance, colloidal metal or color latex can be used as a labeling substance, for example. Representative examples of colloidal metal include colloidal metal particles that are the disperse particles of gold sol, silver sol, selenium sol, tellurium sol, platinum sol, etc. With regard to the size of such a colloidal metal particle, the diameter thereof is generally between approximately 3 and 60 nm. Representative examples of color latex include synthetic latexes such as polystyrene latex colored with a pigment of red, blue, or other colors. As such latex, natural latex such as natural rubber latex can be used. With regard to the size of such color latex, the diameter thereof can be selected from the size ranging from approximately several tens of to several hundreds of nm. Commercially available products can be directly used as such coloring substances. However, there may also be cases where such a commercially available product is further processed, or where a coloring substance can also be produced by a known method.

The antibody of the present invention or a secondary antibody thereof can be bound to a coloring substance by a common method. When such a coloring substance is a gold colloidal particle that is the disperse particle of gold sol, for example, it is generally possible that the aforementioned antibody will be physically bound to the gold sol by mixing them at room temperature.

As a labeling substance, affinity labeling substances (e.g. biotin, etc.) or isotopic labeling substances (e.g. $^{125}$I, etc.) can be used, as well as the aforementioned substances.

In the method of the present invention, an α2,6-sialyl residue-containing glycoprotein can be detected or measured by ELISA, Western blotting, immunoprecipitation, slot or dot blot assay, immunohistological staining, radio immuno assay (RIA), fluoroimmunoassay, an immunoassay using an avidin-biotin or streptoavidin-biotin system, etc. These methods are well known to persons skilled in the art.

When Western blotting is applied, for example, a glycoprotein can be detected by the method described in Example 2 of the present specification.

In addition, when an antibody such as haptoglobin can be used, quantification can be carried out by the following sandwich lectin ELISA method or a common sandwich ELISA method. A plate used in ELISA has previously been coated with an anti-haptoglobin antibody. Thereafter, haptoglobin contained in a sample is trapped on the plate. According to the sandwich lectin ELISA method, the trapped haptoglobin is allowed to react with biotinylated lectin (SNA, SSA, TJA, etc.). For detection, the resultant is allowed to react with streptavidin-horseradish peroxidase (HRP). On the other hand, according to a common sandwich ELISA method, an antibody, which differs from the antibody that has been applied onto a plate, is used for detection. In this case, an antibody used for detection (or a Fab fragment thereof) that is directly labeled with horseradish peroxidase can be used in the reaction. (Otherwise, a secondary antibody labeled with horseradish peroxidase can be used.) In both types of ELISA methods, a coloring substrate is added to develop a color, and the concentration of the color is then measured using a spectrophotometer. A calibration curve has previously been produced with a standard sample containing a known concentration of haptoglobin. Using such a calibration curve, a quantitative value can be calculated.

The agent for diagnosing Alzheimer's disease of the present invention can also be provided in the form of a diagnostic kit. For example, such a diagnostic kit may comprise: (1) lectin for detecting an α2,6-sialyl residue-containing glycoprotein; and/or (2) an antibody against a 180-kD glycoprotein, 95-kD glycoprotein or 40-kD glycoprotein that contains a 2,6-sialyl residue (e.g. an anti-haptoglobin antibody for detecting a 40-kD glycoprotein, etc.). The diagnostic kit may further comprise a secondary antibody to which a labeling substance capable of generating signals has bound, as well as the aforementioned components. Examples of a secondary antibody used herein include an antibody capable of binding to the aforementioned primary antibody and an antibody capable of recognizing an α2,6-sialyl residue-containing glycoprotein and binding thereto (however, which recognizes a site differing from the binding site of the primary antibody and binds thereto). When an antibody capable of recognizing an α2,6-sialyl residue-containing glycoprotein and binding thereto is used as a secondary antibody, sandwich immunoassay (e.g. sandwich ELISA, etc.) can be carried out.

In the diagnostic kit of the present invention, the primary antibody of the present invention may have previously been solid-phased, or it may have previously been labeled with a labeling substance. The type of a solid phase used in the diagnostic kit of the present invention is not particularly limited. Examples of such a solid phase include polymers such as polystyrene, and insoluble carriers such as glass beads, magnetic particles, a microplate, a filter used in immunochromatography, or a glass filter.

The diagnostic kit of the present invention may further comprise other types of any given components. Examples of such other types of any given components include an enzyme used in labeling, a substrate thereof, a radioisotope, a luminescent substance, a fluorescent substance, a coloring substance, a buffer, and a plate, but examples are not limited thereto.

Also, the form of the diagnostic kit of the present invention is not particularly limited. For the purpose of quickly and simply making diagnoses, the diagnostic kit of the present invention can be provided in the form of an integral-type diagnostic kit, wherein constituents for the diagnostic kit of the present invention are integrated. The form of such an integral-type diagnostic kit is not particularly limited. Examples of the form of such an integral-type diagnostic kit include a cassette-type kit used in immunochromatography and a cartridge-type kit used in competitive immunoassay.

The present invention will be more specifically described in the following examples. However, these examples are not intended to limit the scope of the present invention.

EXAMPLES

Example 1

Detection of α2,6-Sialyl Residue-Containing Glycoprotein by Lectin-Blotting Method A human serum or plasma sample (corresponding to 20 μg of protein) was mixed with a Laemmli sample buffer, and the mixture was then heated. Thereafter, the mixture was subjected to SDS/PAGE using 4/20% gradient polyacrylamide gel. Electrophoresis was performed at a constant current of 40 mA for 55 minutes. The separated protein was electrically transcribed onto a PVDF membrane at a constant current of 260 mA for 50 minutes. Thereafter, the membrane was blocked in 1% bovine serum albumin (BSA)-phosphate buffered saline (PBS) for one or more hours. Thereafter, biotinylated lectin (SSA) diluted with 1% BSA-PBS was allowed to react with the PVDF membrane for 1 hour. (In this experiment, biotin-SSA (#300442; Seikagaku Corp.) was used in a concentration of 1 μg/ml.) The membrane was washed three times with 0.05% Tween 20 (surfactant) in PBS for 15 minutes for each time. Thereafter, the resultant was allowed to react with streptavidin-horseradish peroxidase conjugate (HRP) (#RPN1231V; Amersham) diluted with 1% BSA-PBS for 1 hour. Thereafter, the membrane was washed again with a washing solution three times for 15 minutes for each time. A chemoluminescent substrate SUPERSIGNAL WEST DURA extended duration substrate (Pierce)) was used, and the band of an α2,6-sialyl residue-containing glycoprotein was detected by a lumino-image analyzer (LAS-1000plus; Fuji Film, Tokyo), followed by quantification. The results are shown in FIG. 1. The results demonstrated that a 180-kD glycoprotein, a 95-kD glycoprotein, and a 40-kD glycoprotein, which contain α2,6'-sialyl residue, were increased in patients suffering from Alzheimer's disease.

Example 2

Western Blotting Method

Taking into consideration the fact that such glycoproteins contain α2,6-sialyl residue and the molecular weights thereof, an attempt was made to identify a 180-kD glycoprotein, a 95-kD glycoprotein, and a 40-kD glycoprotein. An antibody reacting with a human serum glycoprotein used as a candidate was purchased and examined. As a result, it was found that the 40-kD glycoprotein is haptoglobin. A detection method thereof will be described below.

A human serum or plasma sample (corresponding to 0.04 μg of protein) was mixed with a Laemmli sample buffer, and the mixture was then heated. Thereafter, the mixture was subjected to SDS/PAGE using 4/20% gradient polyacrylamide gel. Electrophoresis was performed at a constant current of 40 mA for 55 minutes. The separated protein was electrically transcribed onto a PVDF membrane at a constant current of 260 mA for 50 minutes. Thereafter, the membrane was blocked in 5% skimmed milk-0.1% Tween 20 in Tris buffered saline (TBS) for one or more hours. Subsequently, a rabbit anti-human haptoglobin antibody (Sigma H-8636) (12 μg/ml) diluted with 3% skimmed milk-TBS at a ratio of 1:1,000 was allowed to react with a nitrocellulose membrane for 1 hour. Thereafter, the membrane was washed three times with 0.1% Tween 20 (surfactant) in TBS for 15 minutes for each time. Thereafter, the resultant was allowed to react with anti-rabbit IgG, horseradish peroxidase (#NA934V; Amersham) (1 μg/ml) diluted with 3% skimmed milk-TBS at a ratio of 1:1,000 for 1 hour. Thereafter, the membrane was washed again with a washing solution three times for 15 minutes for each time. A chemoluminescent substrate SUPERSIGNAL WEST DURA extended duration substrate (Pierce)) was used, and the band of an α2,6-sialyl residue-containing glycoprotein was detected by a lumino-image analyzer (LAS-1000plus; Fuji Film, Tokyo), followed by quantification. The results of the Western blotting using an anti-haptoglobin antibody are shown in FIG. 2. An increase in haptoglobin was confirmed in Alzheimer's disease. A calibration curve has previously been produced with a standard sample containing normal human serum or a known concentration of haptoglobin (#H0138; Sigma). Using such a calibration curve, a quantitative value can be calculated.

BRIEF DESCRIPTION OF THE DRAWINGS

FIG. 1 shows human serum that was stained with SSA lectin.

FIG. 2 shows detection of a 40 kD-glycoprotein with a haptoglobin antibody.

INDUSTRIAL APPLICABILITY

In the present invention, an α2,6-sialyl residue-containing glycoprotein, which exists in a large amount in blood, is used as a marker. Thus, it is possible to make diagnoses using only a trace amount of blood sample: When compared with the conventional diagnostic methods using cerebrospinal fluid or a large amount of blood, a lesser burden is imposed upon a subject. In addition, in the present invention, a special antibody is not required, and lectin that can be prepared in a large amount in an inexpensive way or antibodies that can be easily produced (e.g. anti-haptoglobin antibody, etc.) are used. Accordingly, a method for screening many analytes with high sensitivity can be easily established.

The invention claimed is:

1. A method for diagnosing Alzheimer's disease in a human subject, which comprises:
   (i) measuring the amount of an α2,6-sialyl residue-containing glycoprotein contained in a sample from the subject, wherein said measuring is performed by contacting the sample with a lectin that specifically binds to α2,6-sialic acid and contacting the sample with an anti-haptoglobin antibody to measure the amount of α2,6-sialyl residue-containing glycoprotein in the sample, and
   (ii) comparing the amount of the α2,6-sialyl residue-containing glycoprotein in the sample with the amount of α2,6-sialyl residue-containing glycoprotein in a control sample,
   wherein an increase in the amount of the α2,6-sialyl residue-containing glycoprotein in the sample from the subject compared to the amount of the α2,6-sialyl residue-containing glycoprotein in the control sample indicates a diagnosis of Alzheimer's disease.

2. The method according to claim 1, wherein a 40-kD glycoprotein that contains an α2,6-sialyl residue is detected or measured by an anti-haptoglobin antibody.

3. The method according to claim 1, wherein a 40-kD glycoprotein that contains an α2,6-sialyl residue is detected or measured by sandwich assay using the lectin and an anti-haptoglobin antibody.

4. The method according to claim 1 wherein the sample from a human subject is a blood sample.

5. The method of claim 1, in which the amounts of all of a 180-kD glycoprotein, a 95-kD glycoprotein and a 40-kD glycoprotein are measured.

* * * * *